United States Patent [19]
Lahne et al.

[11] 4,339,413
[45] Jul. 13, 1982

[54] METHANOL-SYNTHESIS REACTOR

[75] Inventors: Ulrich Lahne; Peter Hesse, both of Munich; Erhard Kliem, Wolfratshausen; Bernhard Kruis, Pullach; Reiner Lohmüller, Munich, all of Fed. Rep. of Germany

[73] Assignee: Linde Aktiengesellschaft, Wiesbaden, Fed. Rep. of Germany

[21] Appl. No.: 237,671

[22] Filed: Feb. 24, 1981

[30] Foreign Application Priority Data

Feb. 26, 1980 [DE] Fed. Rep. of Germany ....... 3007202

[51] Int. Cl.³ .............................................. F28D 7/02
[52] U.S. Cl. .................................... 422/200; 165/145; 165/163; 422/211
[58] Field of Search ............... 422/146, 200, 201, 211, 422/216, 173, 202; 165/145, 163

[56] References Cited

U.S. PATENT DOCUMENTS

| | | | |
|---|---|---|---|
| 2,248,993 | 7/1941 | Houdry | 422/200 |
| 3,459,511 | 8/1969 | Jotoku et al. | 422/211 X |
| 3,927,987 | 12/1975 | Winter et al. | 422/200 |
| 4,084,546 | 4/1978 | Schneeberger et al. | 165/145 X |
| 4,263,260 | 4/1981 | Bräutigam | 422/201 |

FOREIGN PATENT DOCUMENTS

| | | | |
|---|---|---|---|
| 2022388 | 11/1970 | Fed. Rep. of Germany | |
| 2504343 | 8/1976 | Fed. Rep. of Germany | 422/201 |

*Primary Examiner*—Richard L. Chiesa
*Attorney, Agent, or Firm*—Karl F. Ross

[57] ABSTRACT

A methanol-synthesis reactor has a housing receiving a catalyst packing and coils of cooling tubes surrounding a core tube and disposed in helical radially spaced layers coaxial with the core tube. According to the invention, the internal diameters of the cooling tubes are from 4 to 50 mm, the distance between neighboring tubes in a direction transverse to the axis and the direction of fluid flow through the catalyst packing is between 2 and 20 times the smallest longitudinal dimension of the catalyst particles and the distance between neighboring tubes measured in the direction of the synthesis gas flow is less than 10 times the transverse distance.

7 Claims, 6 Drawing Figures

METHANOL-SYNTHESIS REACTOR

FIELD OF THE INVENTION

Our present invention relates to a methanol-synthesis reactor and, more particularly, to a reactor which is cooled by a fluid and in which synthesis gas reacts to form methanol exothermally.

BACKGROUND OF THE INVENTION

The synthesis of methanol ($CH_3OH$) from a synthesis gas consisting predominantly of carbon monoxide (CO) and hydrogen ($H_2$) can be carried out ctalytically on a wide variety of catalysts in particulate, granular or other form in a reactor which comprises a housing containing a packing of the catalyst, cooling tubes spaced apart within the catalyst body, and means for passing a coolant (e.g. water) through the cooling tubes and for passing the gas mixture generally axially through the packing.

Since the methanol-synthesis reaction is highly exothermic, the use of cooling tubes in spaced-apart relationship within and in intimate contact with the catalyst body is important to prevent overheating of the synthesis gas and the reaction product entrained therein and the catalyst material as well.

It is known to provide the cooling tubes so that they run generally transversely to the direction of gas flow, e.g. in the form of layers of helical coils surrounding a core tube so that the turns are generally transverse to the synthesis gas flow direction.

A reactor of this type is described in German Open Application DE-OS No. 25 04 343. The cooling-tube arrangement shown and described in this publication prevents the exothermally generated heat of the reaction from shifting the reaction kinetics to the point that undesired reaction products are produced.

Further investigations with reactors of the aforedescribed type have shown that they are not always effective in abstracting the exothermally generated heat to preclude the formation of undesired products or to ensure a high efficiency in the production of methanol.

It appears that the hot reaction products are not always cooled sufficiently and that the reaction cannot be properly controlled merely by providing large numbers of tubes, tube layers or high coolant flow rates. To date, the only effective way of solving the problem has been to overdimension the reactor which increases the quantity of catalyst material for a given volume rate of flow of the synthesis gas and results in increased process operating costs as well as increased capital expenditure for the reactor. Even these expedients are not always satisfactory.

OBJECTS OF THE INVENTION

It is the principal object of the present invention to provide an improved methanol-synthesis reactor.

Another object of the invention is to overcome the drawbacks hitherto encountered with methanol-synthesis reactors of the type described and to provide a reactor which is capable of achieving high productivity at limited operating and capital cost and freedom from technological disadvantages characterizing earlier systems.

SUMMARY OF THE INVENTION

We have now discovered, quite surprisingly, that there is a critical set of geometric and dimensional considerations which influence the operation of a reactor of the type in which tube coils are in contact with and cool a bed of a methanol-synthesis catalyst in a reactor in which the bed is traversed axially by the synthesis gas, and that by maintaining geometric and dimensional conditions within certain limits, it is possible to provide a highly compact, high efficiency reactor which is comparatively small in spite of a high throughput and, especially, eliminates to a significant degree the problem of undesired by-product formation.

More specifically, we have found that there is a critical relationship between the internal diameters of the circular-cross-section tubes and the transverse and axial spacings thereof which, if maintained, bring about the advantages referred to above.

According to the invention, the internal or clear diameters of the tubes must lie between 4 and 50 mm, the distance a between neighboring tubes as measured in a direction transverse to the axial direction of synthesis gas flow must be between 2 and 20 times the smallest longitudinal dimension of the catalyst particles used in the packing, and the distance c between neighboring tubes in the synthesis gas flow direction must be smaller than $10 \cdot a$.

When the tube coils are disposed along helices in respective layers around a core tube in the generally cylindrical upright reactor, the distance a is measured between the outermost part of one layer and the innermost part of another layer radially, i.e. in an axial plane through the reactor intersecting the layers. This dimension is thus the radial spacing between successive layers, i.e. in an axial plane through the reactor intersecting the layers. This dimension is thus the radial spacing between successive layers, i.e. is the radial free space between them.

Correspondingly, the distance c may be the distance between successive turns in the gas flow direction of a given layer and when, as noted below, the spacing c varies along the layer, the mean value of this spacing ($c_m$) should be smaller than $10 \cdot a$. The distance c can be the distance between successive turns of a single helical winding when each layer is formed by a single such winding. However, each layer may be formed by a plurality of windings. The distance c or the distance $c_m$ is thus the axial open space between successive turns.

While in the preferred and best mode embodiment of the invention, the tubes lie in helical coils in respective layers as described, it is also possible to provide them in the form of linear sections with the axes of the tubes perpendicular to the synthesis gas flow direction.

Although the particles can have any shape, it is preferred to utilize polyhedral particles in the catalyst body of the present invention and, most advantageously, bodies which are in the form of regular polyhedra. The particles can be prismatic and in the best mode embodiment of the invention have a cubic shape, the smallest longitudinal dimension corresponding to that of an edge of the cube.

When the particles are hollow or solid cylinders, the smallest dimension can be either the diameter or the length, whichever is less, and when the particles are spherical the dimension referred to will be the diameter. If the particles are of conical configuration, the dimension which determines the transverse spacing of the tubes will either be the diameter or the altitude of the conical body, whichever is smaller.

Within the aforestated ranges for the tube internal diameter and the tube spacing a and c, the particular dimension chosen may be determined by the reaction parameters, such as temperature of the cooling fluid, composition of the synthesis gas, reaction pressure, reaction temperature and catalyst so as to bring about an optimum methanol-synthesis reaction.

Not only does the geometry of the system of the invention provide an especially effective heat transfer from catalyst packing and the reaction gas with the cooling fluid, but the entire reactor can be made significantly more compact, without affecting throughput and productivity, than earlier systems. The result is achieved with significantly less cooling surface area than that of earlier reactors. Obviously this results in a saving of cost and weight as well.

In the preferred and best mode embodiment, the internal diameter of the tubes is between 10 and 30 mm, the distance a is between 10 and 40 mm and the distance c is less than 400 mm. In a more highly preferred construction, the distance a is between 15 and 20 mm and the distance c is at most 30 mm.

According to another aspect of the invention and one which contributes to a considerable extent to an optimum temperature distribution over the path of the methanol-synthesis gas, the distance c between the neighboring tubes in the direction of synthesis gas flow is varied in this direction. This arrangement permits the cooling surface area per unit reactor volume to be varied in order to compensate for variations in the local heat evolution by the exothermic reaction.

The variation of the distance c within a layer can be a progressive variation. The distance can increase continuously over the entire length of the synthesis gas path although it has also been found to be advantageous to provide a progressive increase followed by a progressive reduction and even to repeat a sequence over the length of the path so that the distance reaches two or more maxima or minima along the length of the synthesis gas path.

In another preferred embodiment of the invention, this distance can be constant within a zone of a particular length in the direction of synthesis gas flow although the distance can be stepped from zone to zone in this direction.

BRIEF DESCRIPTION OF THE DRAWING

The above and other objects, features and advantages of the present invention will become more readily apparent from the following description, reference being made to the accompanying drawings in which.

SPECIFIC DESCRIPTION

Figure 1:
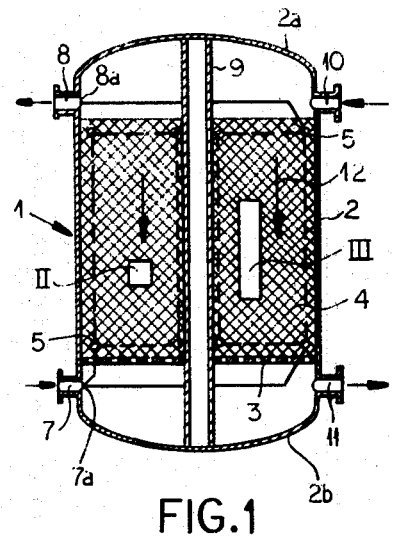
FIG. 1 is an axial cross-sectional view in highly diagrammatic form, of a methanol-producing reactor in accordance with the present invention.

The methanol-synthesis reactor shown in FIG. 1 in its upright position comprises an outer cylindrical housing 2 with domes 2a and 2b at its opposite end, the reactor being filled with a packing 4 of catalyst particles resting upon a perforated plate 3.

Within the body of the packing 4 there is provided an array of cooling tubes 5 through which a coolant, e.g. water, is passed from a coolant inlet 7 communicating with a manifold schematically represented at 7a and connected to the individual tube coils.

At their upper ends, the individual tube coils are connected to a manifold schematically represented at 8a opening into the outlet fitting 8.

The upper dome 2a is formed with a synthesis gas inlet 10 connected to a source of carbon monoxide and hydrogen at the activation temperature for the methanol synthesis reaction.

The bottom dome, below plate 3, is provided with an outlet 11 for the residual reaction gas and methanol produced in the reactor.

The synthesis gas enters through the inlet 10 and is distributed uniformly over the entire cross section of the catalyst packing, passing downwardly in axial flow direction as represented by the arrow 12 such that the exothermic synthesis reaction is carried out within the catalyst bed.

The exothermic reaction heat is abstracted by the cooling tubes of the array 5 and hence a substantially uniform temperature distribution in the catalyst bed in spite of the exothermicity of the reaction.

The gas, now containing methanol vapors, is discharged at 11 and the methanol is condensed or otherwise removed from the gas.

Figure 6:
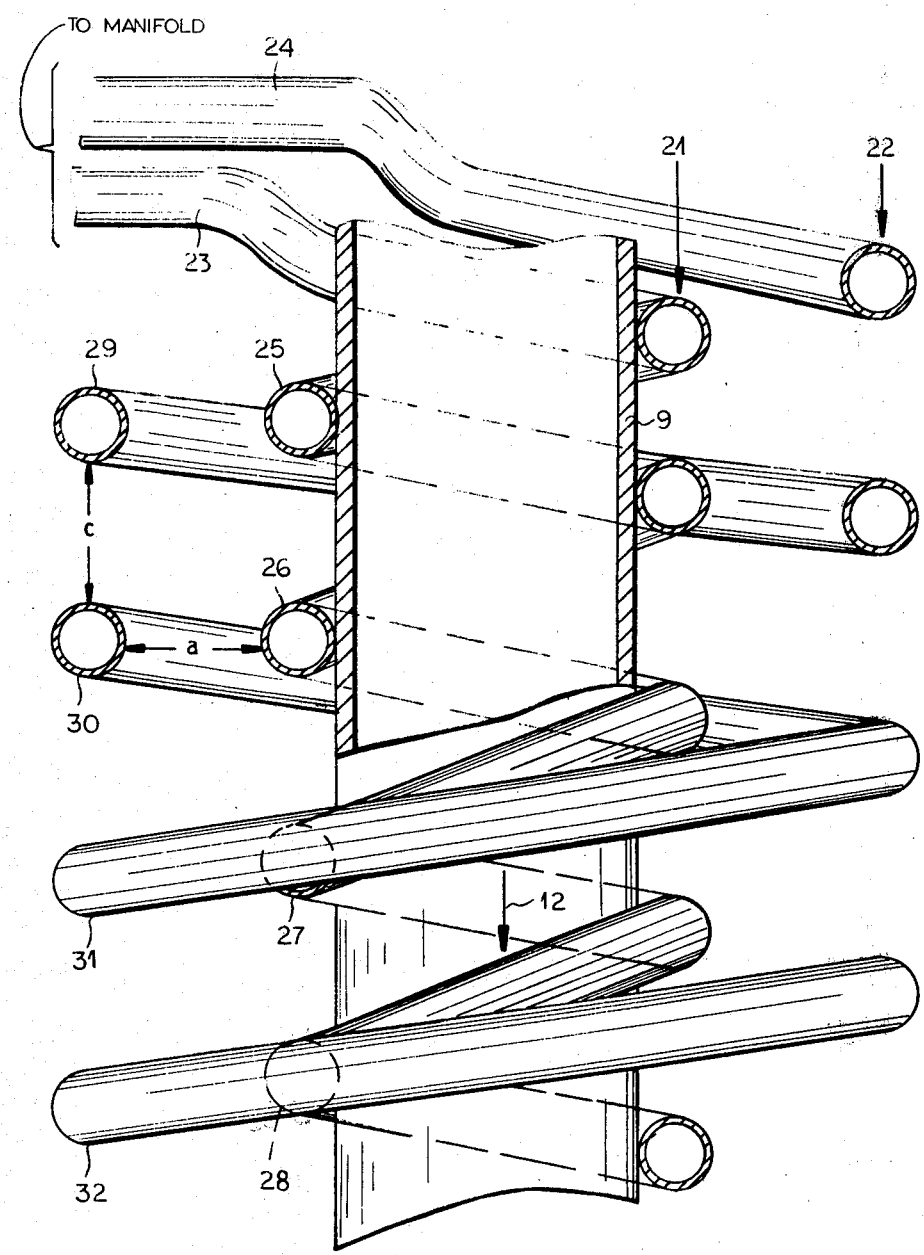
FIG. 6 is an elevational view partly broken away, showing tube coils in accordance with the present invention.

The cooling tubes are disposed in layers 21 and 22, for example, each of which can be composed of one or more helices connected by tube sections 23, 24, for example, to the respective manifold. As shown in FIG. 6, each layer 21 or 22, etc., is made up of a single tube coil.

The tube coils are wound around a core tube 9 which is sealed to the upper and lower dome and provides structural support. As is also clear from FIG. 6, each coil has a succession of turns 25, 26, 27, 28 for the coil 21 and a second succession of turns 29 through 32 for the coil 22.

The two coils or layers are separated by a radial spacing a measured in an axial plane of the apparatus and successive turns are separated a distance c also measured in this plane.

Because of the helical nature of the coils, the tubes lie generally transverse to the direction of flow which has also been represented in FIG. 6 by the arrow 12. The packing is not seen in FIGS. 2 through 6 except for the diagrammatic representation of one of the catalyst particles at 15 in FIG. 2.

Obviously it is possible to achieve the transverse relationship of the tube orientation and the direction of synthesis gas flow by other tube arrangements, e.g. utilizing bundles of linearly extending tubes whose axes are perpendicular to the flow direction 12.

Figure 2:
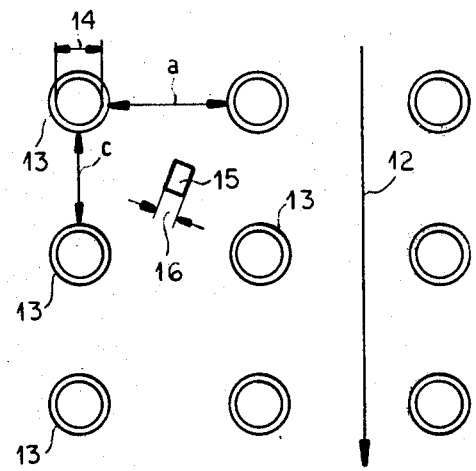
FIG. 2 is a cross section through a number of tubes in this reactor, e.g. in the region of the box II thereof of FIG. 1, showing the geometric distribution and spacing of the tubes, the central plane corresponding to a plane parallel to the direction of gas flow and to an axial plane of FIG. 1.

As can be seen from FIG. 2, which illustrates the tube distribution in the region II of FIG. 1, the tubes 13 are of circular cross section and surrounded by the catalyst particles 15 which can have any conventional configuration although they are preferably cubes, cylinders, balls or Raschig rings.

According to the invention, the internal diameter 14 of the tubes 13 is between 4 and 50 mm (preferably between 10 and 30 mm) while the distance c between neighboring tubes 13 in the flow direction 12 is less than 10·a where a is the distance between two neighboring tubes measured transversely to the flow direction 12. The distance a is between 2 and 20 times the smallest longitudinal dimension 16 of the catalyst particles 15.

The distance a is advantageously between 10 and 40 mm (preferably between 15 and 20 mm) while the distance c is less than 400 mm (preferably at most equal to 30 mm).

Figure 3:
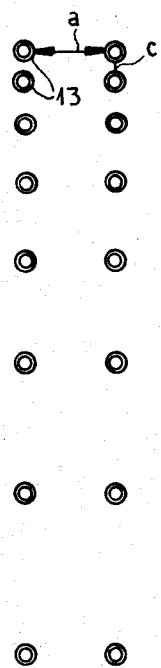
FIGS. 3, 4 and 5 are diagrams showing tube patterns in the direction of gas flow and correspond to the distribution of the tubes in the region III of FIG. 1 which can also correspond to an axial plane through the reactor in the direction of gas flow.
Figure 4:
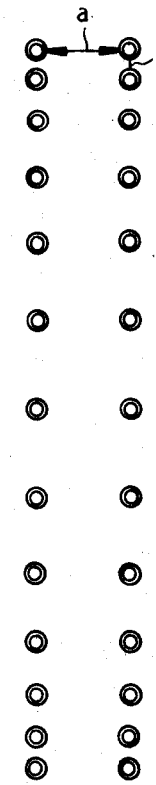
Figure 5:
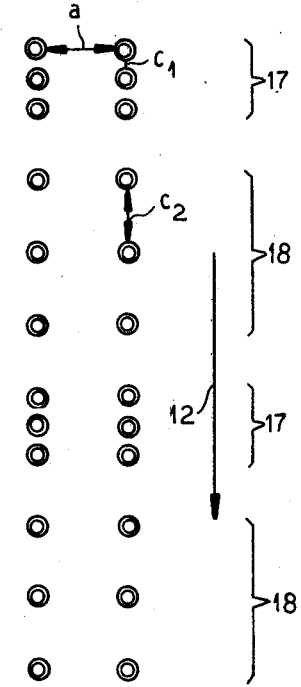

From FIGS. 3 through 5, it will be apparent that the spacing c can vary within the given range in the direction of flow 12. This spacing variation can apply to bundles of linear tubes as well. Preferably the ratio between the wall thickness of the copper tubes and the internal diameter 14 thereof ranges between 0.075 and 0.30.

From FIG. 3 it will be apparent that the distance c increases progressively over the entire height of the tube coil and catalyst bed while the distance a remains constant, and from FIG. 4 it will be apparent that the distance c can increase to a maximum and then decrease progressively.

From FIG. 5 it can be seen that the coils can be broken in the direction of synthesis gas flow into zones 17, 18 which can repeat and in which the distance c is constant for each zone, i.e. at values $c_1$ and $c_2$. In this embodiment as in that of FIG. 4, the distance a remains constant.

We claim:

1. A methanol-synthesis reactor comprising:
   an elongated housing formed with an inlet at one end and an outlet at the opposite end thereof for effecting synthesis gas flow in a predetermined axial direction through said housing;
   means for supporting a gas-permeable body of methanol-synthesis catalyst particles within said housing between said inlet and said outlet;
   an array of coolant tubes spaced apart within said housing, said tubes of said array being spaced from one another in said direction and transversely to said direction; and
   means for feeding a coolant to and removing said coolant from said array of tubes,
   said tubes being of circular cross section with internal diameters between 4 and 50 mm and having a spacing a between neighboring tubes transverse to said direction between 2 and 20 times the minimum linear dimension of the particles of said catalyst, and a spacing c in said direction which is less than 10·a.

2. The reactor defined in claim 1 wherein said internal diameter of said tubes is between 10 and 30 mm.

3. The reactor defined in claim 2 wherein the distance a is between 10 and 40 mm and the distance c is less than 400 mm.

4. The reactor defined in claim 3 wherein said distance a is between 15 and 20 mm and the distance c is at most 30 mm.

5. The reactor defined in claim 1, claim 2, claim 3 or claim 4 wherein the distance c between neighboring tubes in said direction varies therealong.

6. The reactor defined in claim 5 wherein the variation in the distance c in said direction is constant.

7. The reactor defined in claim 5 wherein the distance in said direction is constant over a particular length but varies from length to length in said direction.

* * * * *